United States Patent [19]

Shimomura et al.

[11] Patent Number: 4,904,234
[45] Date of Patent: Feb. 27, 1990

[54] APPARATUS FOR COLLECTING PLASMA

[75] Inventors: Yasushi Shimomura; Masahiko Yamaguchi; Yuuzou Kuromatsu; Koichiro Fukuzaki, all of Ichihara, Japan

[73] Assignee: UBE Industries, Yamaguchi, Japan

[21] Appl. No.: 149,029

[22] Filed: Jan. 27, 1988

[30] Foreign Application Priority Data

Jun. 29, 1987 [JP] Japan ................................. 62-161973
Jul. 17, 1987 [JP] Japan ................................. 62-178728
Jul. 17, 1987 [JP] Japan ................................. 62-178729

[51] Int. Cl.⁴ .............................................. A61M 1/03
[52] U.S. Cl. ................................................... 604/5
[58] Field of Search .......................................... 604/5-6

[56] References Cited

U.S. PATENT DOCUMENTS 4,501,785 2/1985 Nakanishi ....................... 210/500.36
4,648,866 3/1987 Malbrancq et al. ..................... 605/5
4,708,714 11/1987 Larsson et al. ......................... 604/5

Primary Examiner—Dalton L. Truluck
Assistant Examiner—Denise W. DeFranco
Attorney, Agent, or Firm—Armstrong, Nikaido, Marmelstein, Kubovcik & Murray

[57] ABSTRACT

Apparatus is disclosed for collecting plasma. The blood collected at from a blood access is temporarily stored in a blood reservoir and subsequently allowed to pass through a plasma separator at increased speed per unit time by the action of circulating pump located downstream of the reservoir. The plasma separator is connected at its outlet to a circuit communicating with the blood reservoir, whereby the blood cells substantially free of plasma are combined with a fresh feed of blood from the blood access. Blood cells of higher Ht values, while in blood return, come predominantly out of the plasma separator so that the latter involves no sudden increase in pressure.

4 Claims, 3 Drawing Sheets

APPARATUS FOR COLLECTING PLASMA

BACKGROUND OF THE INVENTION AND RELATED ART STATEMENT

This invention relates to an apparatus suitable for use in the collection of plasma, and more particularly to an apparatus for separating plasma from the blood donated and also returning the remaining blood to the donor.

It is known that the blood being withdrawn from the donor can be passed through a plasma separator at increased flow rate per unit time so as to ensure separating plasma from the blood. Too high flow rate, however, is rather inapplicable as there is a prescribed limit placed on the amount of blood to be collected from the individual donor.

A more advanced system has been proposed to this end as disclosed for instance in Japenese Patent Application Laid-open No. 85950/1986. Such known system involves the collection of blood in extracorporeal circuit including a plasma separator alternately with the return of hemocytes or blood cells to the donor under instrumented and controlled conditions. The blood is separated in the plasma separator into both plasma and hemocyte fluids. The hemocyte fluid, temporarily stored in a blood reservoir, is allowed to return to the donor's vein. Blood collection, during blood return, is brought to a stop and vice versa. However, this prior art system is encountered with certain drawbacks described below.

The hemocyte fluid is a viscous fluid resulting from removal of a part of plasma from the blood and having a large volume index of hemoglobin commonly called the hematocrit value and hereinafter referred to simply as the "Ht" value. While in plasma separation, the hemocyte fluid if forced to return to the donor would enter the plasma separate. This is taken to mean that the separator would become suddenly pressurized at its inlet and outlet portions, leading to blood leakage or hemolysis hazards. This problem may be alleviated or eliminated by the return of blood cells at reduced speed which however is literally time-consuming and totally unpractical.

SUMMARY OF THE INVENTION

It is therefore the primary object of the invention to provide an improved apparatus for collecting plasma which is safe and efficient to operate without involving increase in pressure in the associated plasma separate at its inlet and outlet.

More specifically, the apparatus contemplated by the invention is essentially made up of a plasma separator, a blood reservoir, and a dual-purpose pump for both blood-collecting and blood-returning use. The separator is connected at its outlet to a cicuit extending between the reservoir and the pump, and the reservoir is placed between the separator and the pump. With such arrangement, the blood collected at from a blood access is temporarily stored in the blood reservoir and subsequently allowed to pass through the plasma separate at increased flow rate per unit time by the action of a circulating pump located downstream of the reservoir. The hemocyte fluid thus separated from the plasma is thereafter combined with a fresh supply of blood from the blood access and stored in the blood reservoir to thereby maintain at reduced Ht level the blood admixture to be introduced in the plasma separator. In the course of blood return, hemocytes of higher Ht values come predominantly out of the plasma separator so that the Ht level is held low in the blood reservoir.

This and other objects and advantages of the invention will be better understood from the following description taken in connection with the accompanying drawings in which certain preferred embodiments of the invention are exemplified.

According to one aspect of the invention, there is provided an apparatus for use in the collection of plasma which comprises: (a) a blood access; (b) a plasma separator; (c) a dual-purpose pump for causing the blood access to collect the blood from a donor and also to return to the donor the blood cells partially free of plasma; and (d) a blood reservoir placed between the separator and the pump wherein such plasma separator is connected at its outlet to a circuit extending between the reservoir and the pump.

According to another aspect of the invention, there is provided an apparatus for use in the collection of plasma which comprises: (a) a blood access; (b) a plasma separator; (c) a dual-purpose pump for causing the blood access to collect the blood from a donor and also to return to the donor the blood cells partially free of plasma; and (d) a blood reservoir placed between the separator and the pump wherein such plasma separator is connected at its outlet to a circuit communicating with the reservoir.

DETAILED DESCRIPTION OF THE PREFERRED EMBODIMENTS

Figure 1:
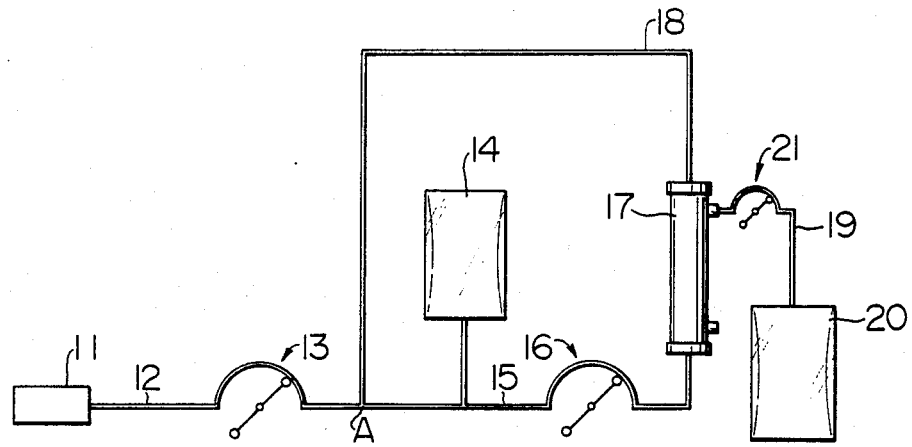
FIG. 1 is a schematic view showing a preferred embodiment of the apparatus of the present invention.

With reference to the drawings and in particular to FIG. 1, there is shown a preferred embodiment of the apparatus according to the invention. This type of apparatus is constructed such that the blood collected at from a blood access 11 is transported through a circuit 12 into a blood reservoir 14 by a dual-purpose or two-way pump 13 serving to act for blood collection and blood return. Upon arrival at a predetermined level in the reservoir 14, the blood is flowed via a circuit 15 into a plasma separator 17 by a circulating pump 16. The blood having entered the separator 17 reaches a plasma-separating membrane which allows plasma alone to pass therethrough, and the plasma thus separated is introduced via a circuit 19 into a plasma reservoir 20 by a collecting pump 21.

The blood cells resulting from removal of a part of plasma from the blood is run through a circuit 18 and combined with a fresh supply of blood collected at a connector point A, and the blood admixture is stored in the reservoir 14.

In the sequence of operation for blood return, the blood is introduced from the reservoir 14 to the separator 17 through the circuit 15 by the pump 16 and treated to separate plasma on the membrane mounted in the separator 17. The resulting plasma is flowed into the reservoir 20 through the circuit 19 by the pump 21.

The blood partially free of plasma is returned via the circuit 12 to the blood access 11 by the pump 13.

Figure 2:
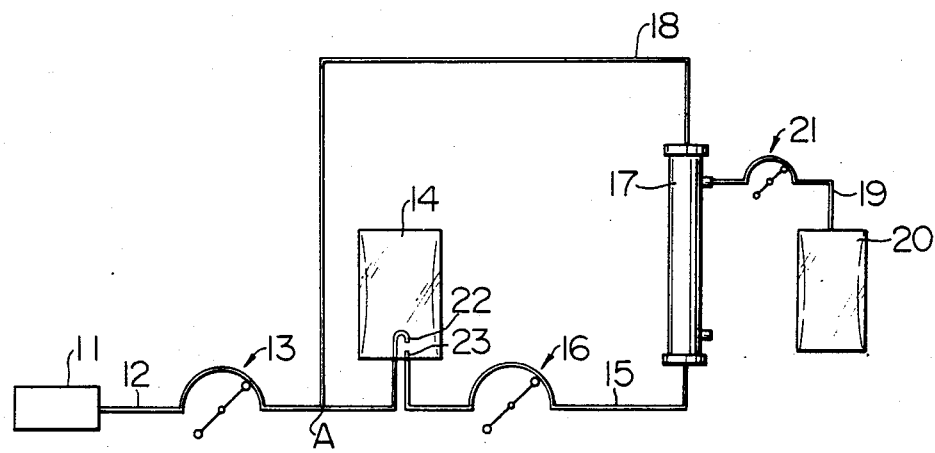
FIGS. 2 and 3 are views similar to FIG. 1, but showing other preferred embodiments of the apparatus.

In another preferred form of apparatus, shown in Fig. 2, the blood reservoir 14 is connected with a blood-incoming circuit and also with a blood-outgoing circuit. The blood-incoming circuit has an opening 22 disposed adjacent to an opening 23 of the blood-outgoing circuit.

Figure 3:
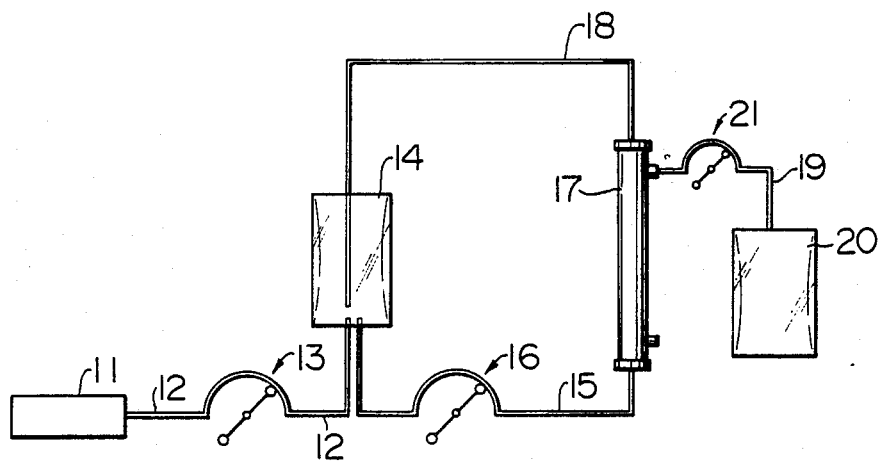

FIG. 3 shows still another preferred form of apparatus in which relatively high Ht blood is allowed to predominantly flow via the circuit 18 into the reservoir 14, followed by admixture with a fresh supply of blood and by storage in the reservoir 14.

In the practice of the invention, suitable amounts of certain anticoagulants should be used to avoid clotting. Anti-coagulant blood circuits and plasma separators if developed could certainly prevent plasma against dilution by the action of anticoagulants.

Eligible anticoagulants are those acceptable for extracorporeal blood circulation and include for example citric acid such as ACD, CPD and the like, heparin, prostagrandins, FOY, MD-805 and the like. These agents may be administered to the donor by injection, by continuous infusion at from the blood access according to the invention or a branched circuit mounted downstream of the blood access, or by instillation.

Examples of the plasma-separating membrane are those capable of high-speed separation and great transmission of plasma proteins. Particularly preferred is a membrane module formed of porous hollow fibers.

Membranes useful in the module may be preferably hydrophilic in nature and also include for example membranes derived by hydrophilizing hydrophobic porous hollow fibers with a surfactant or coating, and membranes resulting from washing of hydrophobic porous hollow fibers with an alcohol which is compatible with water and small in surface tension, followed by filling with physiological saline solution such as sterile water or dust-free water and subsequent replacement with blood just before use.

There is no particular restriction imposed upon the material of porous hollow fibers. Typical examples of the material include polymeric materials such as polyolefines such as high-density polyethylene, polypropylene, poly-4-methylpentene 1 and the like, fluorine-containing polymeric compounds, polysulfone, polycarbonate, polyvinyl chloride, cellulose acetate, polyacrylonitrile, polyvinyl alcohol, polymethylmethacrylate, polyamide and the like, and inorganic materials such as glass, ceramic and similar porous material. Particularly preferred among these are polyolefines for their high resistance to hemolysis.

No particular restriction is imposed on the outer diameter, the peripheral wall thickness and the pore size of porous hollow fibers which however are conveniently about 10–1000 $\mu$m in outer diameter, about 10–500 $\mu$m in peripheral wall thickness and about 0.1–7 $\mu$m in pore size.

The following examples are given to further illustrate the invention, but it is to be noted that the invention is not limited thereto.

EXAMPLE 1

Measurements were made for the Ht values of blood at the inlet and outlet of the plasma separator and also for the Ht values of blood in the blood reservoir under the test conditions given below and with the results shown in FIG. 4.

Figure 4:
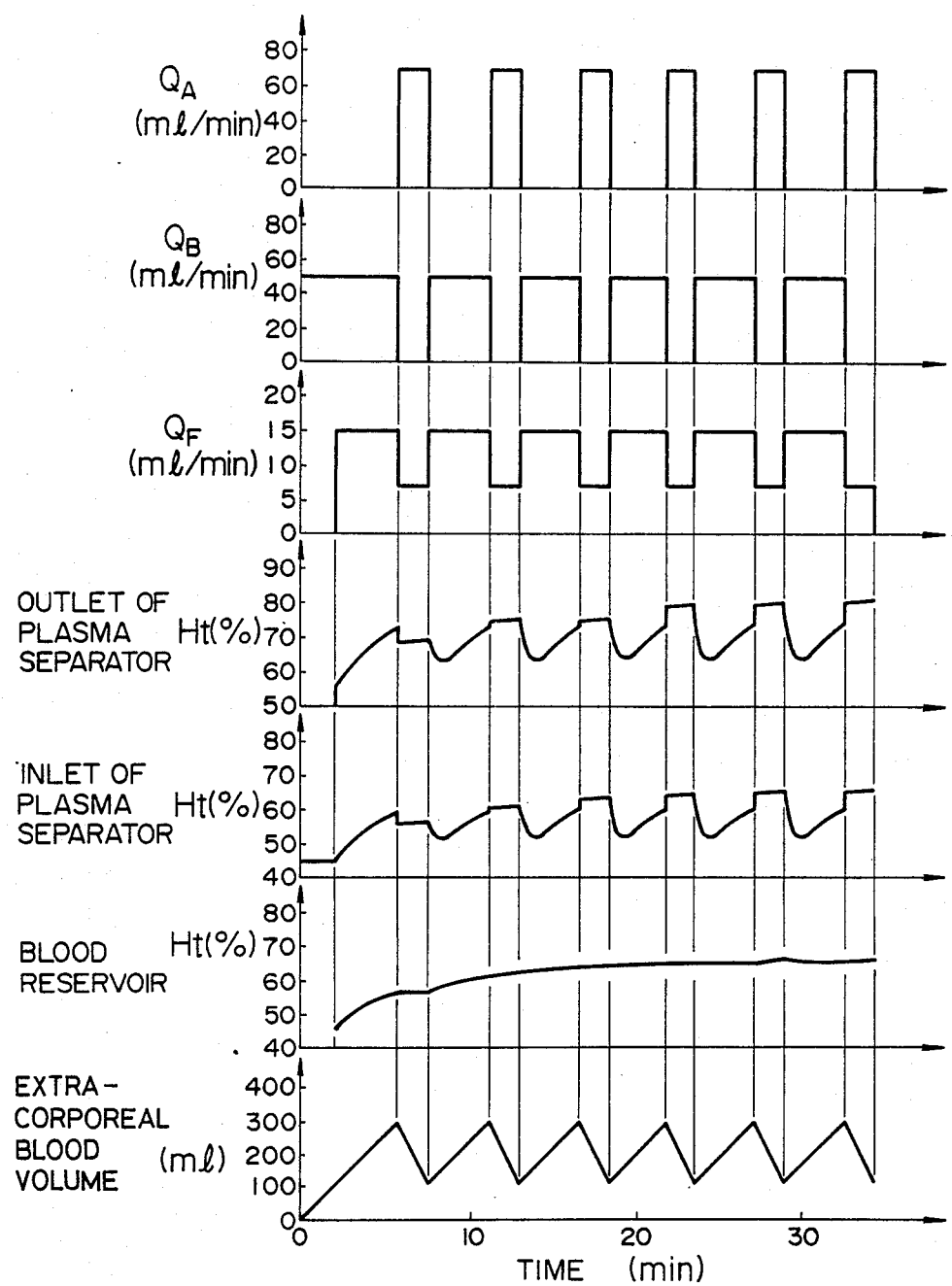
FIG. 4 is a graphic representation of the correlation between the blood flow, the Ht value and the pumping operation.

The test blood was 45% in Ht, and the plasma was collected in an amount of 400 ml by the intermittent pumping operation shown in FIG. 4.
Apparatus: as shown in FIG. 1
Blood reservoir: 400 ml, stretchable
Plasma-separating: polypropylene porous hollow fiber, membrane in blood average pore size 0.37 $\mu$m reservoir outer diameter 400 $\mu$m, inner diameter 300 $\mu$m, void 74% (Ube Industries, Ltd.)
Flow rate of blood: $Q_B$ 50 m./min at collection
Flow rate of blood: 80 ml/min in plasma separator
Flow rate of blood: $Q_A$ 70 ml/min at return
Separation rate of: $Q_F$ 15 ml/min plasma at collection
Separation rate of: $Q_F$ 7 ml/min plasma at return The apparatus representing the invention is highly satisfactory in respect of plasma collection, indicating the Ht values of smaller than 65% at the inlet of the plasma separator after 30-minute separation and the trans-membrane pressures (TMP) of lower than 10 mmHg.

EXAMPLES 2 AND 3

The same procedure of Example 1 was followed except for the use of the apparatus shown in FIGS. 2 and 3.

The apparatus of the invention are highly satisfactory in respect of plasma collection, indicating the Ht values and trans-membrane pressures (TMP) similar to those obtained in Example 1.

It has been confirmed as appears clear from the foregoing results that the apparatus of the invention are all capable of exhibiting reduced hematocrit and hence are safe and efficient to operate.

What is claimed is:

1. An apparatus for use in the collection of plasma from blood comprising:
   a blood access device;
   a dual-purpose pump connected at one side to said device to collect blood from a donor and to return to the donor blood cells partially free of plasma;
   a reservoir connected to the other side of said dual-purpose pump through a tubular conduit;
   said blood access device, said dual-purpose pump, and said tubular circuit defining a blood withdrawal and return flow segment with said reservoir;
   a circulating circuit independently connected to and from said reservoir and having:
   a plasma separator, with a blood inlet, a blood outlet and a plasma outlet, said blood outlet being connected to said reservoir, and
   a circulating pump connected at one side to said reservoir and at the other side to said blood inlet; and
   a plasma circuit connected to said plasma outlet and having:
   a plasma reservoir, and
   a plasma collecting pump interposed between said plasma outlet and said plasma reservoir;
   whereby said blood withdrawal and return flow segment and said circulating circuit are in flow communication only through said reservoir.

2. An apparatus according to claim 1, wherein said plasma separator has porous hollow fibers.

3. An apparatus according to claim 2, wherein materials of said porous hollow fibers are polyolefines.

4. An apparatus according to claim 2, wherein said porous hollow fibers are of about 10–1000 $\mu$m in outer diameter, about 10–500 $\mu$m in peripheral wall thickness and about 0.1–7 $\mu$m in pore size.

* * * * *